United States Patent [19]

Melzig

[11] Patent Number: 5,637,709

[45] Date of Patent: Jun. 10, 1997

[54] PHOTOCHROMATIC SUBSTANCES

[75] Inventor: Manfred Melzig, Wessling, Germany

[73] Assignee: Optische Werke G. Rodenstock, Munich, Germany

[21] Appl. No.: 386,175

[22] Filed: Feb. 9, 1995

Related U.S. Application Data

[63] Continuation of Ser. No. 180,507, Jan. 12, 1994, abandoned, which is a continuation of Ser. No. 46,926, Apr. 13, 1993, abandoned, which is a continuation of Ser. No. 913,980, Jul. 16, 1992, abandoned, which is a continuation of Ser. No. 499,304, filed as PCT/DE88/00620, Oct. 2, 1989, published as WO90/03379, Apr. 5, 1990, abandoned.

[30] Foreign Application Priority Data

Oct. 1, 1988 [DE] Germany .................. 38 33 436.4

[51] Int. Cl.$^6$ ............... C07D 241/38; C07D 451/14; C07D 471/14; C07D 311/96
[52] U.S. Cl. ............... 544/231; 546/18; 549/10; 549/11; 549/331; 549/334; 549/344; 549/345; 549/399; 549/400; 549/404; 549/406
[58] Field of Search ................ 549/406, 407, 549/408, 409, 331, 344, 345, 10, 11, 334, 399, 400, 404; 544/231; 546/18

[56] References Cited

FOREIGN PATENT DOCUMENTS 0246114  11/1987  European Pat. Off. .

OTHER PUBLICATIONS

Thornber, "Isosterism and Molecular Modification in Drug Design", Chemical Society Reviews 8(4) 1979 563–580.

*Primary Examiner*—Phyllis G. Spivack
*Attorney, Agent, or Firm*—Antonelli, Terry, Stout & Kraus, LLP

[57] ABSTRACT

Polychromatic compounds of pyrans having a substituted adamantane or a polycyclic ring system, with the exception of adamantane, in the 2-position of the pyran ring, having the structure

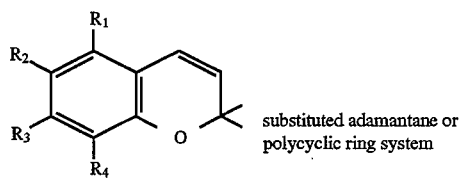

whereby the residues $R_1$–$R_4$ are independently substituents selected from the series H, alkyl, substituted phenyl, phenyl, naphthyl, OH, alkoxy ($C_1$–$C_4$), halogen, alkylamino, dialkylamino, cyan, trifluormethyl, or, $R_1$ and $R_2$ or $R_3$ and $R_4$ or $R_2$ and $R_3$ are constituents of at least one condensed aromatic, heteroaromatic or an alkane ring, wherein said heteroaromatic ring is selected from the group consisting of pyridine, pyrimidine, pyridazine, quinoline, isoquinoline, naphthyridine, quinazoline, quinoxaline, phthalazine, pteridine, phenazine, and benzoquinoline which are substituted by the same residues as $R_1$–$R_4$ above, and wherein the polycyclic ring system is not adamantane and the substituted adamantane contains one or two oxygen, nitrogen or sulfur atoms replacing one or two carbon atoms or is substituted with one or two alkyl moieties.

4 Claims, No Drawings

PHOTOCHROMATIC SUBSTANCES

This application is a continuation application of Ser. No. 180,507, filed Jan. 12, 1994, abandoned, which is a continuation of application Ser. No. 046,926, filed Apr. 13, 1993, which is now abandoned, which is a continuation of application Ser. No. 913,980, filed Jul. 16, 1992, which is now abandoned, which is a continuation application of Ser. No. 499,304, filed as PCT/DE88/00620, Oct. 2, 1989 published as WO90/03379, Apr. 5, 1990, which is now abandoned.

TECHNICAL FIELD

The present invention relates to photochromatic spiropyrans and spiro-1,3-oxazines.

STATE OF THE ART

Photochromatic spiropyrans are of interest for a great number of technical purposes, i.a. data storage, energy conversion and light protection. Accordingly, publications have been quite numerous in recent years:

Most of these publications relate to indolinobenzopyrans (U.S. Pat. No. 2,953,454, Berman), however structures such as bezoxazelo-(U.S. Pat. No. 3,149,120, Berman) and benzthiazolo-(U.S. Pat. No. 3,320,067, Taylor) as well as benzodiazolospiropyrans (FR Patent 14 51 332, Comp. de St. Gobain) can also be utilized. Other heteroatom ring systems, such as benzodithiolo- and benzoxathiolospiropyrans (Guglielmetti, Helv. Chim. acta 58, 2563 (1975)) and oxazolino- , respectively thiazolidinospiropyrans (Guglielmetti, Bull. Soc. France, 568 (1978)) are also found in the literature.

Spiro linkage to heteroatom-6-ring systems is known from dibenzospiropyrans (U.S. Pat. No. 3,022,318, Berman) and similar benzo-anellated compounds (U.S. Pat. No. 3,413,234, Taylor). Quinolinospiropyrans, however, are no longer photochromatic, because in their case the merocyanine structure is the thermodynamically most stable form (Wizinger, Helv. Chim. acta, 23, 247 (1940)).

Pure hydrocarbon structures, like in adamantanospiropyrans (EP-A 0246 114, Heller) also can be linked to the pyran ring. Furthermore, not spiro-linked benzo- and naphthopyrans (U.S. Pat. No. 3,567,605) are described, which also are photochromatic compounds (EP-A 250 193, Heller) at room temperature.

Photochromatic spirooxazines, particularly indolinospironaphthoxazines have also been known for a long time (U.S. Pat. No. 3,562,172, Ono et al) and are already being commercially utilized in sun-protection lenses made of plastic (Rodenstock Perfalit Colormatic).

However, the patents only contain substituted indolinospirobenz- and -naphthoxazines (PCT/DE 84/00275) or such, in which nitrogen replaces one or several CH-groups in the aromatic rings (EP-A 0 141 407 (Kwak) and EP-A 0 245 020 (Rickwood)).

When the aforementioned compounds are employed, by way of illustration, in sun-protection lenses made of plastic material, however, with many of these compounds problems crop up with regard to darkening and lightening behavior and the longevity of the photochromatic effect.

Experiments conducted in accordance with the present invention with photochromatic benzo- and naphthopyrans, which are not spiro-linked, have shown that these are not suited for the intended application. Compounds, such as those described, e g., by Becker, possess at normal temperatures (5°–40° C.) not only in solution, but also in polydiethyleneglycolbisallylcarbonate, a plastic material often utilized for ophthalmic lenses, such a fast inverse reaction that the equilibrium concentrations attainable with natural illumination strengths (10–100 Klux) of the longwave-absorbing form are too small to produce preceivable darkening, respectively a change in color.

The pyrans described in EP-A 0 250 193 absorb in the desired wavelength range of between approx. 450 and 700 mm, moreover colorings are attained in the plastic material at normal temperatures, which suffice for sun-protection purposes. However, longevity is completely insufficient even if protection measures (U.S. Pat. No. 4,720,356, Chu) corresponding to the present state of the art are applied. The reaction of the lenses doped with these compounds already becomes distinctly weaker after darkening and lightening a few times; furthermore the resulting photoproducts give these lenses an additional, irreversible coloring.

Suited for commercial application for sun-protection purposes—as was recognized in accordance with the present invention—are only pyrans, which are linked in the 2-position via a spirocarbon atom to a second cycle. Simple ring systems, e.g. cycloalkanes, however, do not yield photochromatic compounds at room temperature. Only greatly space-fillingly substituted monocycles and polycycles are under certain conditions suitably photochromatic.

Some adamantanospiropyrans of EP-A 0 246 114 are visibly photochromatic at normal temperature, but the inverse reaction into the colorless form is partly too fast for the goal aimed at and, furthermore, the sensitivity of the effect to temperature is too high.

On the other hand, substituting H-atoms in the 3-position of the pyran ring with —$CH_3$, —$C_6H_5$ and —Br yields compounds, which are not photochromatic. Substituting H-atoms in the 4-position, however, accelerates the inverse reaction in such a manner that the photochromatic coloring can only be observed at temperatures far below 0° C.

Furthermore, the following problem arises when the aforementioned compounds are utilized in sun-protection lenses, in partiuclar, which are made of plastic material:

In order to attain a specific coloring, by way of illustration, a neutral gray or brown color, it is frequently necessary to apply several different photochromatic substances, which absorb in different wavelength ranges, together into the material of the sun-protection lens and/or onto the material of a protective lacquer, in particular made of polysiloxan, applied onto the sun-protection lens, thus, however, requiring that the different substances behave as "similarly" as possible with regard to their darkening and lightening behavior and as far as possible also regarding the longevity of the photochromatic effect.

DESCRIPTION OF THE INVENTION

The object of the present invention is to provide a number of different compounds, which absorb at different wavelength ranges, and the darkening and lightening behavior of which is similar so that these compounds, by way of illustration, can be utilized for sun-protection lenses and, in particular, that several of these compounds can used together in a sun-protection lens in order to attain a specific color in the darkened state.

A solution in accordance with the present invention is set forth in the patent claims hereto, the present invention being based on the knowledge described in the following section, the application of which to the compound classes set forth in the claims hereto leads to compounds, the darkening and lightening behavior of which is not only similar, but also permits employing two or several compounds, which absorb in different wavelength ranges, in one sun-protection lens.

The invented introduction of a N-atom in the 3-position with the formation of a 1,3-oxazine ring does not only improve the kinetic behavior considerably, but also results in distinctly improved longevity. The affinity of the pyran ring toward an oxidative attack, representing the lifetime-limiting side reaction of photochromatic compounds of this class in plastic lenses, is distinctly reduced by the electron affinitive influence of the nitrogen atom. This effect is also attained in a somewhat weaker form by introducing nitrogen atoms into the aromatic nuclei anellated to the pyran (oxazine) ring. The adamantanospiropyrido-, -pyrazino-, pyrimidino-, and -pyridazinopyrans (oxazines) formed by this means and the greater homologous -chinolino, -isoquinolino-, -quinoxalino-, -quinazolino-, -phthalazino- and -phenanthrolinopyrans (oxazines) are distinguished, in addition, by markedly improved coloring behavior compared to pure carbon aromatics. Due to the polar character, higher coloring speeds and/or concentrations of the photochromatic dyestuffs are possible in the conventionally applied surface diffusion coloring and thereby permit fabricating lenses which darken much greater.

In this sense, it is also extraordinarily advantageous if the polycycle is substituted by groups, which increase the polarity and/or polarizability. In this event, the inductive electron reduction of the pyran ring has a longevity increasing effect similar to electron affinitive substituted adamantan.

Polycycles, which due to their structure or substitution, stabilize the positive charge transmitted to this molecule part too greatly when the ring is opened following exposure to light, form the opposite boundary. As the open form becomes the thermodynamically favored one, these compounds only occur in the merocyanine form, reversibility of the coloring is no longer given. At least for the plastic materials polymethylmethacrylate and polydiethyleneglycolbisallylcarbonate, substitution with nitro groups is not recommended, because such compounds have side reactions with the matrix when exposed to light, which result in permanent yellow-brown to red-brown discoloring of the lenses.

In particular, according to claim 1 hereto an adamantanospiroheteroaromatic pyran with the following general formulas is suggested:

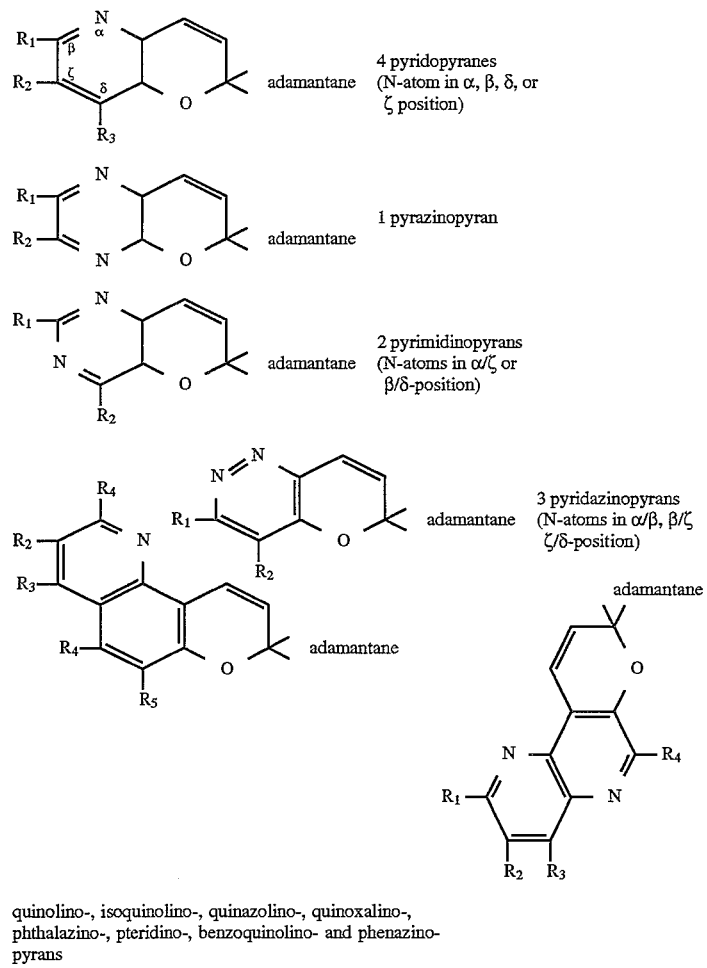

quinolino-, isoquinolino-, quinazolino-, quinoxalino-, phthalazino-, pteridino-, benzoquinolino- and phenazino-pyrans whereby $R_1$–$R_5$: is a substituent from the series H, alkyl, aryl, subst. phenyl, naphtyl, heteroaryl, OH, alkoxy ($C_1$–$C_4$), halogen, alkylamino, dialkylamino, cyan and trifluormethyl, or $R_1$ and $R_2$ or $R_3$ and $R_4$ or $R_2$ and $R_3$ are a constituent of a condensed aromatic or heteroaromatic ring or an alkane ring with 4–8 C-atoms.

These compounds may also have a polycyclic ring system with the exception of adamantane in the 2-position of the pyran ring.

And according to claim 2 hereto an adamantaneospiro (1.3) oxazine of the general formula is suggested:

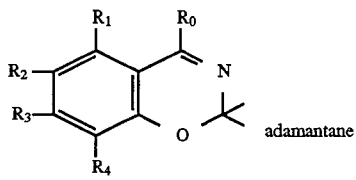

whereby

- $R_0$ is a substituent from the series H, halogen, O-alkyl, N-alkyl,
- $R_1$–R4: is a substituent from the series H, alkyl, aryl, subst. phenyl, naphthyl, heteroaryl, OH, alkoxy (C–$C_4$), halogen, alkylamino, diathylamino, cyan and trifluormethyl, or
- $R_1$ and $R_2$ or $R_3$ and $R_4$ or $R_2$ and $R_3$ are a constituent of a condensed aromatic or heteroaromatic ring or an alkane ring with 4–8 C-atoms.

Furthermore, these compounds may also have a polycyclic ring system with the exception of adamantan in the 2-position of the oxazine ring.

According to claim 3 hereto, the spirobenzo-, -naphto-, -phenanthro- and N-heterocyclopyrans or oxazines according to claims 1 to 3 hereto may have a substituted adamantan in the 2-position of the pyran or oxazine ring.

These invented photochromatic, respectively phototropic, substances have a similar darkening and lightening behavior, which makes it possible to utilize them, by way of illustration, for sun-protection lenses.

DESCRIPTION OF THE PREFERRED EMBODIMENTS

In the following section various examples of the invented compounds will be discussed:

In principle, a number of methods of synthesis are suited for producing the invented heterocyclic-anellated spiro (adamantan-2,2'-(2H)-pyrans).

Synthesis Method a)

The reaction of ethinyl-adamantyl-chloride or -acetate with aza-phenols, respectively, -naphthols. In the following section, the synthesis method is presented schematically and by way of illustration, whereby the production of the compounds needed for the individual steps is made more apparent:

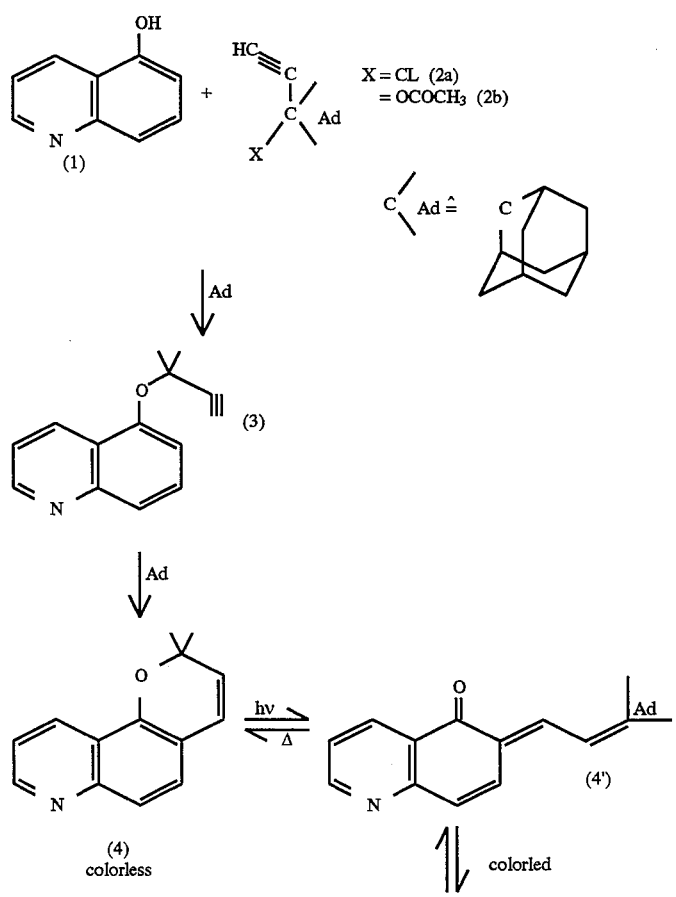

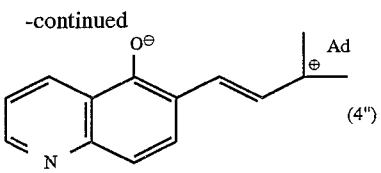

In the following section the description of the individual compounds needed in the aforegoing synthesis method a) are made apparent for example 1.

Preparation of Compound (2b):

A solution of 92 g lithiumacetylide-ethylenediamine complex in 150 ml absolute dioxane is submitted into an 1 l three-necked flask provided with a dropping funnel, magnetic stirrer and gas inlet pipe. Dry acetylene is passed through the solution in a light flow. For approximately 90 min. 150 g adamantaneon in 450 ml absolute dioxane is dripped thereto. The dripping speed is set in such a manner that 60° C. is not surpassed. After dripping has ended, it is stirred at approx. 55° C. for another 15 h. The cooled solution is poured into a mixture of 1 kg ice and 300 ml 5% NaCl solution. The pH-value is set at 5 with diluted HCL and is extracted twice with 250 ml ether each time. The extract is dried with $Mg_2SO_4$ and filtered. After distillation of the ether, 137 g of a whitish solid substance remain. Following recrystallization from acetone/hexane, this solid substance has a melting point of 102°–104° C.

128 g of the ethinyl-adamantane-2-ol are boiled with 60 ml acetic anhydride, 60 ml pyridine and 32 ml acetylchloride for 90 min. under reflux, poured onto a mixture of 750 g ice and 750 g acetone, diluted with water to 2 l and extracted three times with 250 ml ether. After drying with $Na_2SO_4$, filtering and distillation of the ether, a yellowish oil remains. When left to stand for a length of time or pulverized with some pentane, an ivory colored solid material crystallizes, which has a melting point of 64°–65° C. after recrystallization (acetone/hexane).

This solid material has the following NMR data:

$^1H$: δ: 2.64 (s, 1H, ≡CH); 2.05 (s, 3H, $CH_3$)

Preparation of Compound (2a):

The preparation of the ethinyl-adamantyl-2-ol is as made apparent under (2b).

37 g ethinyl-adamantyl-2-ol are dissolved in 200 ml dry benzol. While being stirred and cooled to 15°–20° C., thionylchloride is dripped to it in great excess (250 ml). Then it is stirred for another 3 h (hours) at room temperature under exclusion of moisture. Following the distillation of thionylchloride and the solvent at the rotavap, 34 g of a yellow oil remain, which can be used for further synthesis without additional purification.

Preparation of Compound (4): 12 g Na is dissolved in 300 ml abs. EtOH in a 2 l three-necked flask with a stirrer and drip funnel and reflux cooler and 72 g 5-hydroxy-chinoline (product of the firm Aldrich) dissolved in 600 ml abs. EtOH is poured into the solution. 100 g of the chloride (2) are diluted with 100 ml abs. EtOH and then dripped into the alcoholate solution under vigorous stirring. After the dripping has stopped, it is boiled for 5 h under reflux. The cooled solution is diluted with 1 l ice water and extracted with ether. The organic phase is first washed with diluted NaOH, then with water, dried with $Na_2SO_4$ and filtered. The ether is distilled from the filtrate at the rotavap. The residue contains the raw propargylic ether, i.e. compound (3) of the preceding method of synthesis.

The rearrangement according to Imai and Ide (Chem. pharm. Bull. 10, 926 (1962)) requires high pressures and temperatures, the process proposed in EP-A 0 246 114 with acidic $Al_2O_3$ as the catalyst requires high temperatures. These result in a high percentage of not more closely examined side products. In accordance with the present invention, the process according to Koch-Pomeranz et al. (Helv. chim. acta. 56, 2981 (1973)) is, therefore, preferred:

80 g of the propargylic ether (3) and 25 g silver tetrafluoroborate, dissolved in 500 ml chloroform are stirred at room temperature for 8 h. After shaking out with 10% aqueous KCN solution, the organic phase is dried with $Na_2SO_4$. The remaining residue following distillation of the solvent is chromatographed with toluol as the solvent and $Al_2O_3$ as the adsorbant. Remaining are 9.2 g spiro (adamantan-2,2'-(2H)-pyrano(6,5-f) quinoline), i.e. the compound designated (4). Following recrystallization from $CHCl_3/C_6H_{12}$, a light sand-colored solid substance is yielded, which has a melting point (mp) of 246° C. The solution in $CH_2Cl_2$ exposed to light has an orange color ($\lambda_{max}$=442 nm).

In the same manner, the compounds given as examples 2 were produced from the commercially available hydroxy-aza-aromatics. In the following examples, the parent compound used is given first and then the yielded end compound.

EXAMPLE 1

5-hydroxyquinoline (parent compound) spiro (adamantane-2,2'-(2H) pyrano (6,5-f) quinoline), mp: 246° C.

EXAMPLE 2

4-hydroxyquinoline (parent compound) spiro(adamantan-2,2'-(2H) pyrano (5,6-C quinoline), mp: 219° C.

EXAMPLE 3

8-hydroxyquinoline (parent compound) spiro(adamantan-2,2'-(2H) pyrano(5,6-h) quinoline), mp: 223° C.

EXAMPLE 4

2-hydroyquinoxaline (parent compound) spiro (adamantan-2,2'-(2H) pyrano (5,6-b)-quinoxaline), mp: 151° C.

EXAMPLE 5

4-hydroxyquinaldine (parent compound) spiro (adamantan-2,2'-(2H) pyrano (5,6-c) 2"-methyl-quinoline), mp: 179° C.

EXAMPLE 6

8-hydroxyquinaldine (parent compound) spiro (adamantan-2,2'-(2H) pyrano (5,6-h) 2"-methyl -quinoline), mp: 162° C.

EXAMPLE 7

5-hydroxyisoquinoline (parent compound) spiro (adamantan-2,2'-(2H) pyrano (6,5-f) isoquinoline), mp: 229° C.

EXAMPLE 8

2-hydroxpyridine (parent compound) spiro(adamantan-2, 2'-(2H) pyrano (6,5-b) pyridine), mp: 154° C. (Z.)

EXAMPLE 9

3-hydroxpyridine (parent compound) spiro(adamantan-2, 2'-(2H) pyrano (6,5-c) pyridine), mp: 178° C.

EXAMPLE 10

4-hydroxypyridine (parent compound) spiro(adamantane-2,2'-(2H) pyrano (5,6-c) pyridine), mp: 166° C.

EXAMPLE 11

4-hydroxypyrimidine (parent compound) spiro (adamantane-2,2'-(2H) pyrano (6,5-d) pyrimidine), mp: 142° C. (Z.)

EXAMPLE 12

3-hydroxy-6-methyl-pyridine (parent compound) spiro (adamantane-2,2'-(2H) pyrano (6,5-c) 6"-methylpyridine mp: 139° C. (Z.)

(Z.: decomposition)

The o-hydroxy-aza-aromatics of examples 1, 4, 5, 8, 10 and 11 are partially present in the tautomeric -on-form (1H-pyridone, etc.). This makes formation of the propargylic ether more difficult.

Alltogether the afore-described methods of synthesis have, despite easy access to the parent compounds (1), disadvantages as the output of compound (3) is partially very small ($\leqq 10\%$). Experiments with ethinyl-adamantyl acetate as compound (2b) analogous to examples 16 and 17 of EP-A 0 246 114 yielded, in general, even worse results.

Method of Synthesis b)

The reaction of o-acetyl-hydroxy-aza-aromatics with adamantaneon, subsequently reduction and dehydration to 2H-pyran.

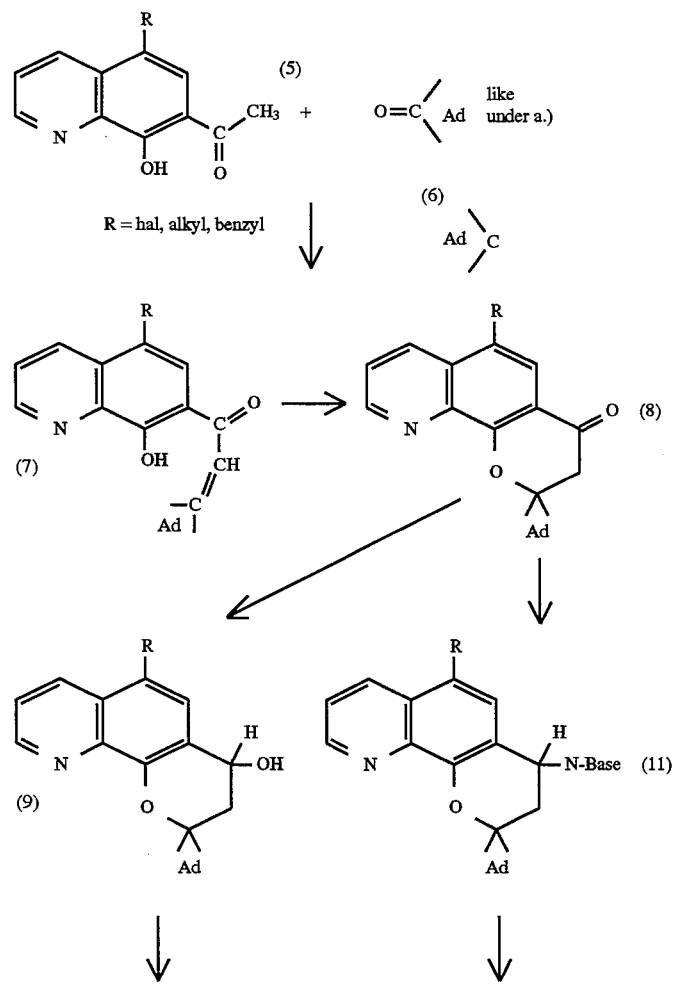

-continued

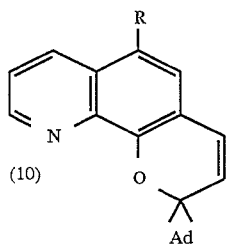 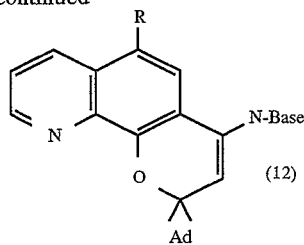

N-base = piperidino, morpholino, diethylamino, pyrrolidino

In the following section the preparation of the individual compounds necessary in the aforegoing method of synthesis b) are made apparent, by way of illustration, for example 13.
Preparation of Compound (5):

The o-acetyl-hydroxy-aza-aromatics are accessible according to the known methods (cf. examples 13–21), usually with good yields.
Preparation of Compound (8):

50 g of 7-acetyl-8-hydroxy-5-methyl-chinoline and 50 g adamantanone were boiled with 250 ml toluol and 20 ml pyrrolidine for 3 h under reflux. The reaction water formed was removed at the water separator. The toluol in the black-brown solution is distilled at the rotavap. The oily residue is thoroughly shaken with 2 ml conc. HCl in 200 ml methanol. After distillation the methanol, 76 g of a dark brown oil, namely compound (8), are left.
Preparation of Compound (9):

15 g of compound (8) are dissoloved in 300 ml n-butanol in a 500 ml three-neck flask with a magnetic stirrer and reflux cooler and 30 g $NaBH_4$ are added in small amounts. After this addition, it is boiled for 3 h. After the butanol has been destilled, the residue is dissolved in 250 ml $H_2O$ and extracted with $CH_2Cl_2$. The organic extract is dried with $MgSO_4$ and filtered. After distillation of the $CH_2Cl_2$, 8 g of a black oil remain. This is chromatographed with neutral $Al_2O_3$ as the adsorbent and $CH_2Cl_2$/hexane as the solvent (rising from 1:5 to 5:2). 6.1 g of an ocher-colored solid substance, namely compound (9), can be gained from the main fraction following withdrawal of the eluent.
Preparation of Compound (10):

6 g of compound (9) are carefully fused in a round flask with 3 g waterfree $CuSO_4$ and is retained as a fusion for approx. 15 min. It is recommended to put on an air-cooler as under circumstances the substance (10) partialy sublimates. Cooler and cooled, finely ground fusion are washed with $CHCl_3$, respectively extracted. The organic extract is dried with $MgSO_4$ and filtered. After distillation of the solvent, 4.6 g of an orange-yellow oil remain. This oil is chromatographed in the same manner as explained in the preparation of compound (9). Left is 3.9 g of a light yellow substance with a melting point of 214° C., namely compound 10.

Examples 14–21 are produced in an analogous manner.

EXAMPLE 13

7-acetyl -8-hyroxy-5-methyl-quinoline (parent comp.(5)) E. Hodel, U.S. Pat. No. 3,113,135, spiro(adamantane-2,2'-(2H) pyrano-(5,6-h)-5"methylquinoline), mp: 214° C.

EXAMPLE 14

7-acetyl-8-hydroxy-5-chlor-quinoline (like 13) spiro (adamantane-2,2'-(2H) pyrano-(5,6-h)-5"-chlorquinoline), mp: 182° C.

EXAMPLE 15

7-acetyl-8-hydroxy-5-benzyl-quinoline (like 13) spiro (adamantan-2,2'-(2H) pyrano-(5,6-h)-5"-benzylquinoline), mp: 133° C. (Z.)

EXAMPLE 16

7-acetyl -8-hydroxy-5-chlor-quinaldine (like 13) spiro (adamantan-2,2'-(2H) pyrano-(5,6-h)-5"-chlor-2"-methylquinoline, mp: 166° C. (Z.)

EXAMPLE 17

7-acetyl8-hydroxy-5-methyl-quinaldine (like 13) spiro (adamantan-2,2'-(2H) pyrano-(5,6-h)-2", 5"-dimethylquinoline, mp: 174° C. (Z.)

EXAMPLE 18

3-acetyl-4-hydroxy-quinoline F. Kroenke et al., Ann. 644, 93 (1961); the substance yielded is identical to that of example 2

EXAMPLE 19

4-acetyl3-hydroxy-pyridine W. H. Hunter, DE-A 2 014 779 the substance yielded is identical to that of example 9.

EXAMPLE 20

2-acetyl-3hydroxy-pyridine according to T. Yamazaki et al., Chem. Pharm. Bull, 1150 (1977) spiro(adamantan-2,2'-(2H) pyrano-(5,6—6) pyridine) mp: 150° C.

EXAMPLE 21

3-acetyl -4-hydroxy-6-methyl-quinoline M. S. Mayadeo, Ind. J. Chem. 599 (1984) spiro(adamantan-2,2'-(2H)-pyrano-(5,6-c)-6"-methylquinoline) mp: 227–229° C.

The use of approximately equimolar or larger amounts of secondary amines as condensation aids in reaction (7)→(8) results in 4-substituted pyranones (II) being the principle products. These permits dehydration in the same manner as the 4-hydroxypyranes (compound (9).

In this case, the nitrogen-base-substituted 2H-pyrans given below have worse longevity compared to the unsubstituted compounds.

EXAMPLE 22 spiro(admantan-2,2'-4'-pyrrolidino-(2H) pyrano(5,6-h)-5"-methylquinoline) mp: 226° C. (Z.)

EXAMPLE 23 spiro(admantan-2,2'-4'-piperidino-(2H) pyrano(5,6-h)-5"-methyl-quinoline) mp: 217° C. (Z.)

EXAMPLE 24 spiro(adamantane-2,2'-4-piperidino-2(H) pyrano (5,6-h)-5"-chlorquinoline) mp: 169° C. (Z.)

As the subsequent state of the art for the following examinations listed herein, the substances of examples 1,4 and 14 of EP-A 0246 114 were synthesized in accordance with the information described therein.

Reference 1: spiro(adamantane-2,2'-(2H) benzopyran)

Reference 2: spiro(adamantane-2,2'-4"-chlor-naphtho (2,1-e) (2H)pyran)

Reference 3: spiro(adamantane-2,2'-4'-pyrrolidino-(2H) benzopyran)

The invented compounds and the reference substances were utilized in a lacquer as set forth in DE-OS 3 156 568 (in a concentration of 4%) for coloring 2 mm thick plane lenses made of polydiethyleneglycolbisallylcarbonate. This substance, also known under the trade name CR-39 of the firm PPG, is the most commonly used polymer for plastic lenses in the world.

The lenses fabricated by this means were measured spectrally. The characteristic value is the optical density at the point of the longwave absorption maximum $\lambda_{max}$ (approx. 420–470 nm) of a lens exposed to 60 Klux at 23° C. for 15 minutes according to DIN 58217. In order to attain the unexposed state, the lenses were baked out at 85°–90° C. for 30 minutes, left to cool 30 minutes in the dark and then measured.

$\Delta OD = OD\lambda_{max}$ (exposed to light) $- OD\lambda_{max}$ (unexposed)

The lenses were exposed to approx. 130 Klux in an exposure test apparatus (Suntest of the firm Original Hanau) at 40° C. until the reaction of the lens $\Delta OD$ returned to 1/e of its original value. The exposure time LD determined in this manner is a measure of the longevity of the photochromatic effect of a lens in normal use.

$\Delta OD\ (o) = e\ ^{*}\Delta OD\ (LD)$

TABLE 1

| Example | ΔOD (o) | LD (h) |
|---|---|---|
| 1 | 0.624 | 26.2 |
| 2 | 0.314 | 35.1 |
| 3 | 0.472 | 22.2 |
| 5 | 0.265 | 28.4 |
| 6 | 0.392 | 15.8 |
| 7 | 0.577 | 25.7 |
| 9 | 0.332 | 12.2 |
| 10 | 0.308 | 13.4 |
| 12 | 0.250 | 16.9 |
| 14 | 0.688 | 24.9 |

TABLE 1-continued

| Example | ΔOD (o) | LD (h) |
|---|---|---|
| 15 | 0.281 | 11.4 |
| 16 | 0.252 | 15.2 |
| 20 | 0.279 | 23.3 |
| 21 | 0.419 | 23.7 |
| 22 | 0.316 | 7.1 |
| 24 | 0.298 | 6.4 |
| Reference 1 | 0.459 | 8.4 |
| Reference 2 | 0.644 | 14.2 |
| Reference 3 | 0.433 | 2.6 |

The superiority of the invented substances with regard to longevity of the photochromatc effect is apparent. The 2H-pyrans substituted in the 4-position with a nitrogen base (example 22–24) are distinctly worse in point of longevity, yet superior to the immediately comparable compounds of the state of the art (reference 3).

The introduction of nitrogen atoms into the benzo-, respectively naphto-, ring system anellated to the (2H)-pyran ring reduces the electron density therein. The nitrogen bases in the 4-position of the (2H) pyrane ring increase its electron density. This raises, respectively reduces, as proven in accordance with the present invention, the longevity of the photochromatic effect.

Even more effective is the introduction of a nitrogen atom into the 2H-pyrane ring itself.

In the following section, the synthesis of the (2H) 1,3-benzoxazine principle structure is described. For this purpose, a salicylic acid amide (13) and adamantanone (6) (cf. H.O.L. Fischer, Ber. 65, 1032 (1932) form the basis. Depending on the further reaction, different 4'-substituted spiro(adamantane-2,2'-(2H)-1'-3'-benzoxazines) can be synthesized.

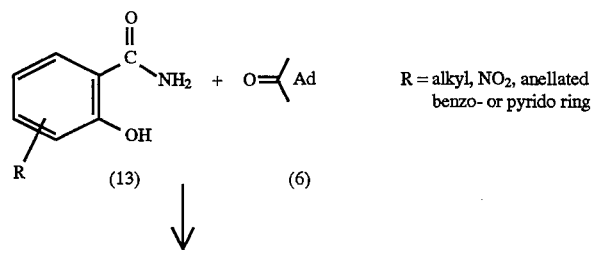

R = alkyl, NO₂, anellated benzo- or pyrido ring

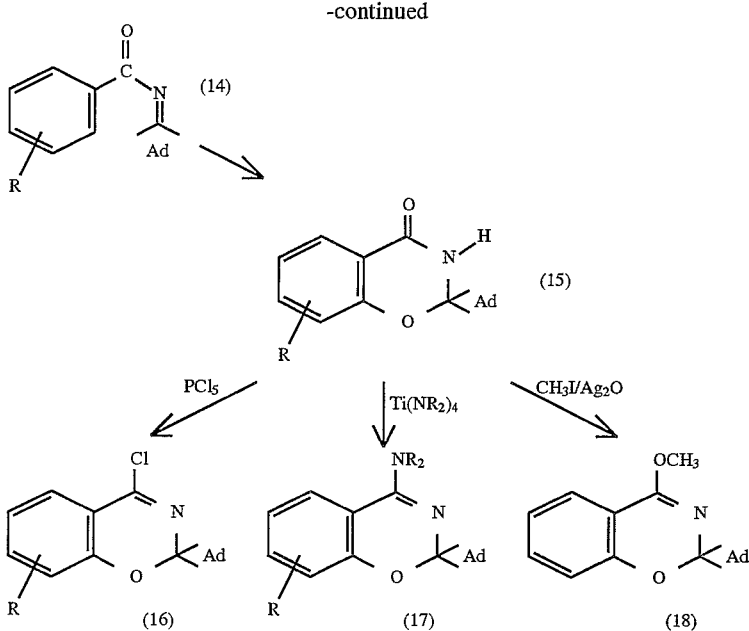

In the following section, the preparation of the individual compounds required in the aforegoing method of synthesis is made apparent, by way of illustration, for example 25.
Preparation of Compound (15):

In a 500 ml flask, 13.7 g salicylamide and 16.8 g adamantanone in 150 ml chloroform are added to 25 g polyphosphate ethyl-ester and boiled under stirring for 5 h under reflux. After the solvent has been distilled, the residue is hydrolyzed with 10% aqueous NaOH. The precipitated crystal masses are collected by suction ground and stirred in 500 ml 8% aqueous NaOH of 35° C. for complete hydrolysis. The filtration is followed by washing with water. The product is recrystallized from acetone/hexane. Light yellow crystals with a mp of 220°–225° C. (Z.), namely compound (15) is yielded.

Preparation of (16):

12.9 g (15) are dissolved in 200 ml absolute benzol and 10.5 g $PCl_5$ are dripped thereto under stirring for 10 min. Subsequently, it is stirred at 75° C. for another 15 min. After the $POCl_3$ and the solvent have been distilled, the imidoyl-chloride remains as a yellow-brown oil. This oil is purified by means of chromatography with neutral $Al_2O_3$ using toluol/hexane (2:1) as the eluant. Yielded are light ocher-colored crystals with a fp of 119° C., namely compound (16).

By using substituted 0-hydroxybenzoic, respectively naphthoic acid amides, further compounds of the same class can be synthesized. If 3-hydroxyisonicotine or 5-nitrosalicylic acid amide are utilized as parent substances, the electron density in the oxazine ring can be additionally reduced.

EXAMPLE 25 salicylic acid amide (parent compound 13) spiro (adamantan-2,2'-(2H)-4'-chlor-1,3'-benzoxazine) (product compound (17)) mp: 119° C.

EXAMPLE 26 m-cresotine acid amide (parent compound 13) spiro (adamantan-2,2'-(2H)-4'-chlor-7'-methyl-1'.3'-benzoxazine) (17) mp: 114° C.

EXAMPLE 27

1-hydroxy-2-naphthoic acid amide (13) spiro(adamantan-2,2'-(2H)-4'-chlor-naphtho (2,1-e)-1',3'-oxazine) (17) mp: 136° C.

EXAMPLE 28

3-hydroxyisonicotine acid amide (13) spiro(adamantan-2,2'-(2H)-4'-chlor-pyrido (4,3-e)-1'.' oxazine) (17) mp: 152° C.

EXAMPLE 29

5-nitrosalicylic acid (parent compound 13) spiro (adamantan-2,2'-(2H)-4'-chlor-6'-nitro-1'.3'-benzoxazine) (17) mp: 130° C. (Z.)

If compound (15) is reacted analogously to the process described by J. D. Wilson (J. Org. Chem 36, 1613 (1971) with tetrakisdialkylaminotitanium (commercially available), cyclic amidines are yielded (compound 17).

The reaction of compound (15) with alkyliodide/$Ag_2O$ in dioxane analogous to H.O:L. Fischer (Ber. 65, 1032 (1932) yields the corresponding 4-alkoxy substituted compounds (18).

As the compounds (17) and (18) have a higher electron density in the oxazine ring compared to the analogous compounds (16) and therefore less light stability, they, as less preferable compounds, are not included in the results of table 2. The latter contains the values of lenses colored with the substances of examples 25–29 in the same manner as described above and subjected to a longevity test.

TABLE 2

| Example | ΔOD (o) | LD (h) |
|---|---|---|
| 25 | 0.304 | 43.4 |
| 26 | 0.236 | 36.2 |
| 27 | 0.277 | 31.8 |
| 28 | 0.228 | 42.6 |
| 29 | 0.416 | 7.4* |

*The permanent brown coloring of the lenses sometimes occurring probably is caused by the reaction of the nitro group with the plastic matrix.

Although the afore-mentioned changes in the pyrane ring system have great influence on the longevity of the photochromatic effect, their influence on the kinetics of the lightening reaction, thus the inverse reaction, in which the pyrane ring is reclosed, is rather small.

Even little modifications in the adamantane part, however, drastically alter the lightening speeds.

This is described below:

The preparation of the substituted admantanons or norbornanons occurs according to the data apparent in the literature. Further synthesis can take place in accordance with one of the methods a or b explained in the introduction hereto.

Adamantan-diones (resin products) and thiaadamantanes (instable under the reaction conditions) cannot be transformed into photochromatic compounds in accordance with either of the methods a and b.

The synthesis of examples 30–33 occurs with 2-acetyl-4-chlor-1-hydroxy-naphthaline according to route b.

According to the papers by I. N. Azerbaev (Vses. Knof. Khim Atsetilena 5th 268, (1975)) and S. A. Baisalbaeva (Deposited Doc. 1983, VINITI 1898–1983), who produced high-substituted ethynyl-adamant-6-oles, the method of synthesis b, however, can be selected.

It is quite apparent that the azaphenols and -naphthols of of the previous description can be combined with the polycycles listed in the following section.

In the following examples, the parent compound is again given first and then the yielded end compound.

EXAMPLE 30

1,3-dimethyl-adamantane-2-one or: 1,3-dimethyl-tricyclo (3.3.1.1$^{3,7}$)-decan-2-on according to D. Lenoir et al., J.A.C.S. 96, 2157 (1974) spiro(1,3-dimethyl-adamantane-2, 2'-4''-chlor-naphtho(2,1-e) (2H)-pyran) mp: 124–127° C. (cyclohexane)

EXAMPLE 31

5,7-dimethyl -adamantane-2-one (like 30) spiro(5,7-dimethyl-adamantane-2,2'-4''-chlor-naphtho(2,1-e) (2H)-pyran) mp: 141°–144° C. (acetone/pentane)

EXAMPLE 32

1,3-diaza-adamantane-2-one J. Kuthan et al., Coll Czech. Chem Comm. 38, 3491 (1973) spiro(1,3-diazaadamantane-2,2'-4''-chlor-naphtho(2,1-e) (2H)-pyran) mp: 149° C. (Z)

EXAMPLE 33 norbornan-7-one or: bicyclo(2.2.1)heptane-7-one P. G. Gassmann, tetrahedron Letters 9 (1963) spiro-(bicyclo (2.2.1)heptane-7,2'-4''-chlor-naphtho(2,1-e) (2H)-pyran) mp: 120–124° C. (cyclohexane)

Plastic lenses were colored with the substances of examples 30–33 and the reference substances 1 and 2 in the previously described manner.

The course of the inverse reaction (4'', respectively 4'→4) was observed in these lenses at $\lambda_{max}$ of the long-wave absorption after 15 min. exposure to 60 Klux at 23° C.

Evaluated was the time that passed until AoD returns to 1/e of the original value.

| Example | Time t (min) |
|---|---|
| 30 | 214 |
| 31 | 38 |
| 32 | 14 |
| 33 | 3.6 |

-continued

| Example | Time t (min) |
|---|---|
| Reference 1 | 32 |
| Reference 2 | 26 |

The substitution of both CH-groups, which are adjacent to the spiro-C-atom of the adamantane, with C—CH$_3$ prevents the inverse reaction very greatly. Substitutions in the 5,7-position have substantially less influence.

The substitution with N accelerates the inverse reaction. The effect may be reduced by the stabilization of the ionic form 4'' (by partial acceptance of the formal positive charge by the nitrogen atoms).

The replacement of the bulky adamantane residue with a substantially smaller norbornane residue is usually accompanied by much quicker lightening of the coloring.

What I claim is:

1. Spirobenzo-, spironaphtho-, spirophenanthro- and spiro N-heterocyclo pyrans having a polycyclic ring system, in the 2-position of the pyran ring, having the structure

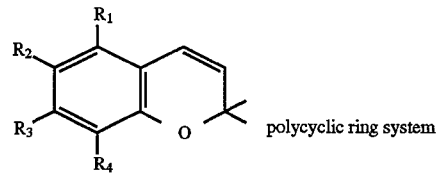

whereby the residues

R$_1$–R$_4$: are independently substituents selected from the series H, alkyl, substituted phenyl, phenyl, naphthyl, OH, alkoxy (C$_1$–C4), halogen, alkylamino, dialkylamino, cyano, trifluormethyl, or R$_1$ and R$_2$ or R$_3$ and R$_4$ or R$_2$ and R$_3$ are constituents of at least one condensed aromatic, heteroaromatic or an alkane ring, with 4–8 carbon atoms, said heteroaromatic ring selected from the group consisting of pyridine, pyrimidine, pyridazine, quinoline, isoquinoline, naphthiridine, quinazoline, quinoxaline, phthalazine, pteridine, phenazine, and benzoquinoline which are substituted by the same residues as R$_1$–R$_4$above and wherein the polycyclic ring system is not adamantane.

2. The compounds according to claim 1, wherein the polycyclic ring system is a bicyclo-, or tricyclo- heptan, -octan or -nonan.

3. Spirobenzo-, spironaphtho-, spirophenanthro- and spiro N-heterocyclo pyranes having a substituted adamantane, in the 2-position of the pyran ring, having the structure

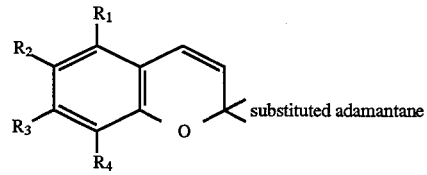

whereby the residues

R$_1$ –R$_4$: are independently substituents selected from the series H, alkyl, substituted phenyl, phenyl, naphthyl, OH, alkoxy (C$_1$–C$_4$), halogen, alkylamino, dialkylamino, cyan, trifluormethyl, or $R_1$ and $R_2$ or $R_3$ and $R_4$ or R2 and $R_3$ are constituents of at least one condensed aromatic, heteroaromatic, or an alkane ring, with 4–8 carbon atoms, said heteroaromatic selected from the groups consisting of pyridine, pyrimidine, pyridazine, quinoline, isoquinoline, naphthiridine, quinazoline, quinoxaline, phthalazine, pteridine, phenazine, and benzoquinoline which are substituted by the same residues as $R_1$–$R_4$ above, and the substituted adamantane contains one or two oxygen, nitrogen or sulfur atoms replacing one or two carbon atoms or is substituted with one or two alkyl moieties.

4. The compounds according to claim 3, wherein the substituted adamantane is 1,3-dimethyl-adamantane, 5,7-dimethyl-adamantane or 1,3-diaza-adamantane.

* * * * *